United States Patent
Baranton et al.

(10) Patent No.: US 9,841,615 B2
(45) Date of Patent: Dec. 12, 2017

(54) METHOD FOR DETERMINING AT LEAST ONE OPTICAL DESIGN PARAMETER FOR A PROGRESSIVE OPHTHALMIC LENS

(71) Applicant: ESSILOR INTERNATIONAL (COMPAGNIE GENERALE D'OPTIQUE), Charenton-le-Pont (FR)

(72) Inventors: Konogan Baranton, Charenton-le-Pont (FR); Thierry Bonnin, Charenton-le-Pont (FR); Juliette Wierzbicki, Charenton-le-Pont (FR); Ahmed Haddadi, Charenton-le-Pont (FR); Sarah Marie, Charenton-le-Pont (FR); Bjorn Drobe, Singapour (SG)

(73) Assignee: ESSILOR INTERNATIONAL (COMPAGNIE GENERALE D'OPTIQUE), Charenton-le-Pont (FR)

( * ) Notice: Subject to any disclaimer, the term of this patent is extended or adjusted under 35 U.S.C. 154(b) by 0 days.

(21) Appl. No.: 15/034,630

(22) PCT Filed: Oct. 28, 2014

(86) PCT No.: PCT/FR2014/052737
§ 371 (c)(1),
(2) Date: May 5, 2016

(87) PCT Pub. No.: WO2015/067876
PCT Pub. Date: May 14, 2015

(65) Prior Publication Data
US 2016/0327813 A1    Nov. 10, 2016

(30) Foreign Application Priority Data
Nov. 8, 2013  (FR) ...................... 13 60991

(51) Int. Cl.
*A61B 3/10* (2006.01)
*A61B 3/00* (2006.01)
(Continued)

(52) U.S. Cl.
CPC ............ *G02C 13/005* (2013.01); *A61B 3/113* (2013.01); *G02C 7/027* (2013.01); *G02C 7/061* (2013.01)

(58) Field of Classification Search
USPC ................................................ 351/200–246
See application file for complete search history.

(56) References Cited

U.S. PATENT DOCUMENTS 6,286,957 B1 * 9/2001 Livnat .................. G02C 13/005
                                                    351/204
8,297,752 B2   10/2012 Wada
(Continued)

FOREIGN PATENT DOCUMENTS

EP    1 747 750 A1    1/2007
FR    2 894 688 A1    6/2007
WO    2012/038676 A1  3/2012

OTHER PUBLICATIONS

International Search Report, dated Mar. 18, 2015, from corresponding PCT application.

*Primary Examiner* — Mohammad Hasan
(74) *Attorney, Agent, or Firm* — Young & Thompson

(57) ABSTRACT

A method for determining at least one optical design parameter for a progressive ophthalmic lens intended to be fitted in a frame of a wearer, depending on the wearer's visual behaviour, includes: a) placing the wearer in a situation in which he carries out a visual task at a first working distance; b) during this task, determining at least two gaze directions of the wearer at this first working distance in a frame of reference of the wearer's head; c) determining a relative position of a surface related to the frame or to an ophthalmic
(Continued)

lens intended to be fitted in the frame; d) determining for each gaze direction at the first working distance the intersection between this gaze direction and the surface so as to establish a map of these points of intersection on this surface; and e) deducing the sought-after optical design parameter from this map.

18 Claims, 1 Drawing Sheet

(51) Int. Cl.
*G02C 13/00* (2006.01)
*A61B 3/113* (2006.01)
*G02C 7/02* (2006.01)
*G02C 7/06* (2006.01)

(56) References Cited

U.S. PATENT DOCUMENTS

| | | | |
|---|---|---|---|
| 2011/0128496 A1* | 6/2011 | Giraudet | G02C 7/027 351/204 |
| 2011/0279773 A1 | 11/2011 | Drobe et al. | |
| 2015/0168743 A1* | 6/2015 | Drobe | G02C 7/065 351/159.42 |
| 2016/0011436 A1* | 1/2016 | Contet | G02C 7/028 351/159.42 |

* cited by examiner

METHOD FOR DETERMINING AT LEAST ONE OPTICAL DESIGN PARAMETER FOR A PROGRESSIVE OPHTHALMIC LENS

TECHNICAL FIELD TO WHICH THE INVENTION RELATES

The present invention relates to a method for determining an optical conception parameter of a progressive ophthalmic lens.

TECHNOLOGICAL BACKGROUND

Ophthalmic progressive lenses allow the wearer to benefit from an optical power compensation that is adapted to various vision distances without changing spectacles. They may also correct other visual defects, such as astigmatism for example.

A progressive ophthalmic lens has a variable power over the surface of the lens.

For example provision is made for a first vision zone for far vision having a first average power value, a second vision zone for near vision having a second average power value and, between these two zones, a third vision zone for intermediate vision, the curvature of which varies gradually and which is called the progression corridor.

The difference between the first and second average power values is equal to the power addition of the lens.

The fitting cross is a reference point for positioning the lens in front of the eye of a wearer, the position of which is predefined by the manufacturer of the lens.

The first zone for far vision is centered on a reference point for far vision, the position of which is predetermined for a given lens by the manufacturer.

The second zone for near vision is centered on a reference point for near vision, the position of which is predetermined for a given lens by the manufacturer.

The first zone for far vision and the second zone for near vision are separated by a distance called progression length.

The progression length may be defined as the vertical distance between the fitting cross and the position of the near-vision reference point defined by the manufacturer of the eyeglass.

The vertical and horizontal directions of the lens are defined depending on the position of the lens under conditions of use by the wearer, in the chosen frame.

The progression length of the lens must be adjusted depending on the fitting height of the ophthalmic lens.

The fitting height of the ophthalmic lens corresponds to the height, relative to the lower edge of the rim of the frame, of the projection of the pupil of the wearer having a predetermined primary gaze direction onto a mean plane of this rim of the chosen frame, corresponding to a mean plane of the ophthalmic lens once fitted into said frame.

This predetermined primary gaze direction corresponds to the gaze direction of the wearer under far-vision conditions.

The progression length of the lens is adjusted so that the second zone for near vision of the lens is included in the lens once edged and positioned in the chosen frame.

Furthermore, the second zone used for near vision may be positioned depending on visual habits of the wearer.

Customarily, the choice of the progression length is made by the optician on the basis of subjective criteria such as the posture of the wearer or feedback given by the latter on his past piece of equipment.

A method for determining the progression distance of a lens is also known from document U.S. Pat. No. 8,297,752, in which method a single far-vision point of the wearer and a single near-vision point of the wearer are determined on the ophthalmic lens and the corresponding progression length is deduced therefrom. An ophthalmic lens suitable for the wearer may thus be selected.

However, it is not certain, by applying this method, that a sufficient portion for comfortable use of the second zone for near vision used by the wearer will be included in the ophthalmic lens once the latter has been edged and fitted in the frame chosen by the wearer. Specifically, generally, the precise determination of the progression length involves a precise determination of the position of the first and second vision zones. The precise positioning of the frame on the face of the wearer, resulting for example from the geometry of the frame and the fit of this frame on the head of the wearer, directly influences the position of the first and second vision zones for a given wearer. These parameters are not taken into account in the prior art.

SUBJECT OF THE INVENTION

In order to remedy the aforementioned drawback of the prior art, the present invention proposes a method for determining at least one optical conception parameter of a progressive ophthalmic lens intended to be fitted into a frame chosen by a wearer, allowing both the particular visual behavior of the wearer and the dimensions of the frame chosen by this wearer to be taken into account, in order to define for the ophthalmic lens the optical conception parameters (optical design) that are the best suited both to the wearer and to the frame.

More particularly, according to the invention such a method is proposed comprising the following steps:

a) placing the wearer in a situation in which he performs a visual task at a first working distance;

b) determining, during this visual task, at least two directions of the gaze of the wearer at this first working distance in a frame of reference associated with the head of the wearer;

c) determining a relative position of a surface or a line associated with said frame or with an ophthalmic lens intended to equip said frame in the frame of reference of the head of the wearer;

d) determining, for each direction of the gaze at the first working distance determined in step b), the intersection between this direction of the gaze at the first working distance and said surface or said line, so as to establish a map of these points of intersection with this surface or this line; and e) deducing from this map said sought optical conception parameter.

The following are other nonlimiting and advantageous features of the method according to the invention:

in step a), the wearer performs a reading or writing task or an interactive task or an observation task;

in step c), said surface is one of the following surfaces: mean plane of the ophthalmic lens, mean plane of a rim of the frame, mean plane of the rims of the frame, back or front face of the ophthalmic lens, or any plane attached to the coordinate system of the frame or of the head;

in step a), the wearer follows with his eyes a target, the position of which is known in a frame of reference associated with an image-capturing device and in step b), using this image-capturing device, an image of the head of the wearer is captured for various positions of the target corresponding to the various gaze directions at the first working distance;

in step b), for each captured image, the position of the rotation center of at least one eye of the wearer is determined in the frame of reference associated with his head and therefrom each direction of the gaze at the first working distance is deduced as being the straight line connecting this rotation center with the target in its corresponding position;

in step b), for each image captured while the wearer is equipped with the frame fitted with ophthalmic lenses, the position of the rotation center of at least one eye of the wearer is determined in the frame of reference associated with the head and therefrom the direction of the gaze at the first working distance is deduced as being the optical path connecting the rotation center of the eye and the target, while taking into account the prismatic deviation of said ophthalmic lens;

in step b), the position of the eye rotation center of the wearer in the frame of reference associated with the head is measured for said captured image;

in step b), the position of the eye rotation center of the wearer is approximately estimated in the frame of reference associated with the head;

in step b), a reference position of the rotation centers of the eyes is measured in the frame of reference associated with the head of the wearer in a preliminary step and this reference position is recorded;

for each gaze direction, a data pair associating the posture of the head and the gaze direction are determined and placed in memory;

in step b), each image of the wearer is captured when the target is found on the optical axis of the image-capturing device;

in step d), the intersection between the direction of the gaze at the first working distance and said surface is determined by directly measuring in the captured image the position of the image of the pupil of the eye of the wearer in the image of the ophthalmic lens;

in step a), the wearer is equipped with the chosen spectacle frame and, in step c), the relative position of said surface or said line is determined from at least one captured image of the head of the wearer during said visual task;

in step c), the relative position of said surface or said line is determined from a database;

in step e), at least one of the following quantities is determined: a mean value of the drop angle of the near-vision gaze, the dimensions and/or the position of a zone of use of the ophthalmic lens containing the positions of all the determined points of intersection, the distribution of the positions of these points of intersection in this zone of use;

in step e), at least one of the following optical conception parameters is determined: progression length and/or inset and/or reading distance and/or position of the near-vision zone;

said gaze directions at the first working distance are spaced apart by at least 5 degrees of angle, preferably 15 degrees of angle for a visual task distributed over a measuring surface of 17 centimeters width by 24 centimeters length and carried out at a working distance equal to 40 centimeters;

in step b), at least four different gaze directions at the first working distance are determined, at least two of which are spaced apart by a non-zero angle in a horizontal direction;

the following steps are furthermore carried out:

a') placing the wearer in a situation in which he performs a visual task at a second working distance;

b') determining, during this visual task, at least one direction of the gaze of the wearer at this second working distance;

in step e), this gaze direction of the wearer at the second working distance is taken into account to determine said sought optical conception parameter;

in step a), the wearer performs a near-vision visual reading task, and in step e), from the map determined in step d), a zone of near-vision use of the lens, and/or an amplitude of the movement of at least one eye of the wearer during the reading task and/or an amplitude of the movement of the head of the wearer during the reading task, and/or an eye-head coefficient equal to the ratio of the amplitude of the movement of an eye of the wearer in a determined direction to the maximum amplitude of the movement of this eye during the reading task are/is deduced.

The invention also relates to a measuring device for implementing the method such as described above, including image-capturing means;

means for displaying a moving target, the position of which is known in a frame of reference associated with the image-capturing device;

which means are programmed to trigger an image capture when the target has a predetermined triggering position on the displaying means.

DETAILED DESCRIPTION OF ONE EXEMPLARY EMBODIMENT

The description which follows with reference to the appended drawings, which are given by way of nonlimiting examples, will make it easy to understand the essence of the invention and how it can be achieved.

In the appended drawings.

It will be noted that identical or corresponding elements of the various ophthalmic lenses shown in projection in the mean plane of the frame in FIGS. 1 to 4 are referenced by the same signs.

Figure 2:
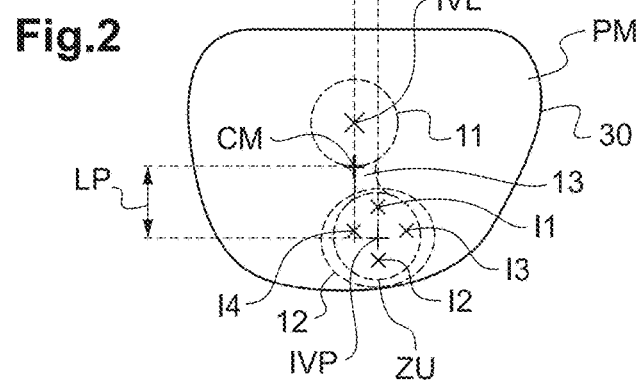
FIG. 2 is a schematic view of the distribution of the points of intersection of various gaze directions with a mean plane of a rim of the frame.
Figures 3, 4:
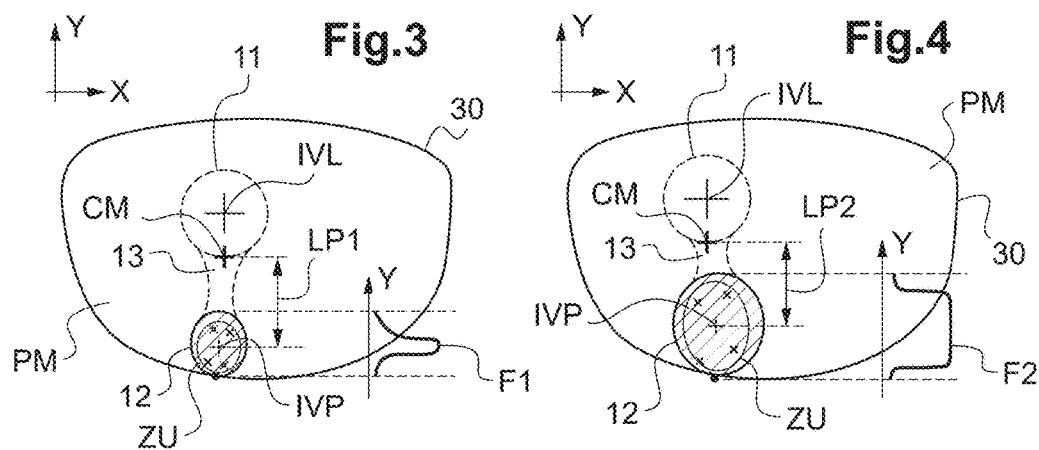
FIG. 3 is a schematic front view of a first exemplary ophthalmic lens in which the near-vision zone of use is located in a first position relative to a far-vision reference point.
FIG. 4 is a schematic front view of a second exemplary ophthalmic lens in which the near-vision zone of use is located in a second position relative to the far-vision reference point.

The lens 30 shown in FIGS. 2 to 4 is an ophthalmic lens having a progressive spherical power addition, or a progressive ophthalmic lens, and includes, in its upper portion, a first vision zone 11, the spherical power of which is suitable for the far vision of the wearer depending on his visual-correction needs and, in its lower portion, a second vision zone 12, the spherical power of which is suitable for the near vision of this wearer.

FIGS. 2 to 4 show the projection of this lens 30 in the mean plane PM of the corresponding rim of the chosen frame 10.

Below, the first zone 11 for far vision will be called the "far-vision zone 11" and the second zone 12 for near vision will be called the "near-vision zone 12"

Between the far-vision zone 11 and the near-vision zone 12 there is, as is known, a third vision zone 13 that is suitable for intermediate distance vision.

The far-vision zone 11 surrounds a far-vision reference point IVL, whereas the near-vision zone 12 surrounds a near-vision reference point IVP.

At the far-vision reference point IVL, the lens 30 has a first predetermined spherical power suitable for the far vision of the wearer, whereas, at the near-vision reference point IVP, it has a second predetermined spherical power suitable for the near vision of the wearer.

The power of the lens varies, preferably continuously, between said far-vision reference point IVL and said near-vision reference point IVP, along a curve called the "principal progression meridian line", which passes through these two points. This principal progression meridian line passes through these three FV, IV and NV zones in an overall vertical direction.

In the context of the present description, the following definitions shall be adopted.

According to standard ISO 13666:2012, the point located on the front surface of a lens, which the manufacturer considers as a reference point for positioning the eyeglass in front of the eye, is referred to as the fitting point.

The position of the fitting point on the lens is predetermined and known.

The fitting height then corresponds to the vertical distance that separates the fitting point from the horizontal tangent passing through the lower point of the periphery of the lens.

In the rest of the description, a zone of use ZU of an eyeglass is defined as being a zone of space representative of a statistical distribution of a set of points on the eyeglass through which the gaze of the wearer passes during a particular visual task, or for use at a predetermined working distance. The zone of use ZU may be defined equivalently either spatially, by a statistical distribution of points I1, I2 over the ophthalmic lens or over another projection plane associated with the ophthalmic lens or with the rim of the corresponding frame, or vectorially, by a statistical distribution of directions A1, A2 of the gaze. Alternatively and more simply, the zone of use ZU may also be defined in tabulated format by a statistical distribution of the drop angles A1, A2 of the gaze in the sagittal plane of the wearer.

The progression length LP of the ophthalmic lens is defined as the vertical distance between the fitting cross CM and the position of the near-vision reference point IVP defined by the manufacturer of the eyeglass (FIG. 2).

The fitting cross CM is a reference point for positioning the lens in front of the eye of a wearer, the position of which is predefined by the manufacturer of the lens.

Other definitions may be adopted for the progression length. It may be expressed relative to the prism reference point or to the far-vision reference point IVL rather than relative to the fitting cross. As the respective positions of these points are moreover also given by the manufacturer, this definition is equivalent to the preceding one.

Whatever the adopted definition of progression length, the method according to the invention remains the same.

The mean surface of the ophthalmic lens is defined as the surface equidistant at every point from the front and back faces of the lens.

The horizontal direction is considered to be perpendicular to the vertical direction, following for example a plumb line.

The direction of the gaze is a straight line belonging to a plane containing the point fixated by the wearer with his gaze and the rotation centers of the eyes.

For one eye in particular, the gaze direction is defined as the straight line connecting the point fixated by the wearer with his gaze and the center of rotation of this eye.

Figure 1:
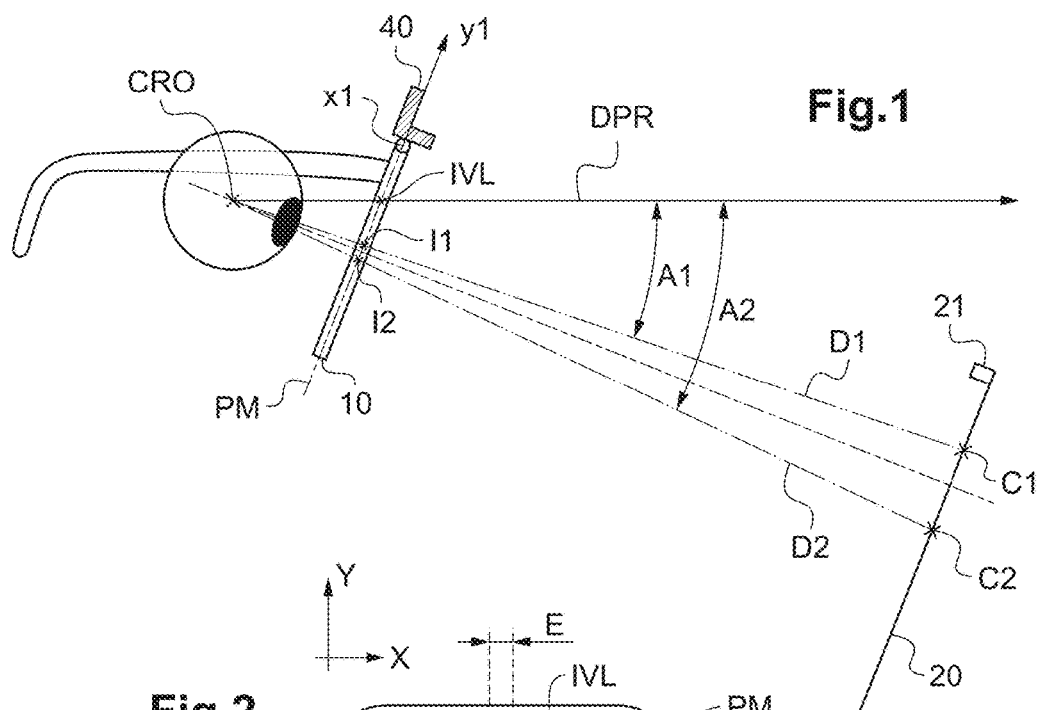
FIG. 1 is a schematic view of one embodiment for determining various gaze directions of the eye of a wearer.

For far vision, with a sighted point straight ahead at infinity, the direction of the gaze is horizontal. This direction of the gaze corresponds to the primary gaze direction DPR (FIG. 1).

The progressive ophthalmic lens is especially defined by two principal optical quantities:
- the addition equal to the variation in power between the far-vision reference point IVL and the near-vision reference point IVP; and
- a "nominal power" equal to the power of said reference point IVL for far vision.

The inset E of the lens is defined as the horizontal offset between the far-vision reference point IVL and the near-vision reference point IVP. The inset E is also called "internal offset"

In order to provide the wearer with the greatest possible visual comfort, it is necessary to precisely position the far-vision and near-vision zones of the two ophthalmic lenses with which this wearer is intended to be equipped so that said wearer looks through the far-vision zone 11 when he is looking far away and through the near-vision zone 12 when he is carrying out a near-vision visual task.

The relative position and the dimensions of these two far- and near-vision zones thus depends on geometrico-physiognomic parameters of the wearer, such as his interpupillary distance for example, and his visual behavior. They also depend on geometric characteristics of the frame chosen by the wearer, especially the height of the rims of the frame, the base of the latter or the pantoscopic angle of the frame worn by the wearer.

By virtue of the method according to the invention, it is possible to determine at least one optical conception parameter of each progressive ophthalmic lens, depending on the visual behavior of the wearer.

This method in particular allows the visual behavior of the wearer to be evaluated in a natural posture during a near-vision visual task and geometrico-morphological parameters of the wearer and the geometry of the chosen frame to be taken into account.

By natural posture, what is meant is the posture that is habitually adopted by the wearer in the absence of any constraint.

This optical conception parameter may in particular be related to the relative position of the far-vision zone 11 and near-vision zone 12.

It is for example a question of the progression length LP; LP1; LP2 of the ophthalmic lens or of the inset E (FIGS. 2 to 4).

More precisely, according to the invention, the following steps are carried out:

a) placing the wearer in a situation in which he performs a visual task at a first working distance;

b) determining, during this visual task, at least two directions D1, D2 of the gaze of the wearer at this first working distance in a frame of reference (x1, y1) associated with the head of the wearer;

c) determining a relative position of a surface PM or a line associated with said frame 10 or with an ophthalmic lens 30 intended to be fitted into said frame 10 in this frame of reference (x1, y1) associated with the head of the wearer;

d) determining, for each gaze direction D1, D2 determined in step b), the intersection between this direction of the gaze at the first working distance and said surface or said line, so as to establish a map of these points of intersection I1, I2, I3, I4 on this surface; and e) deducing from this map said sought optical conception parameter.

Step a)

The wearer is placed in a situation in which he performs a task having at least one visual component at a first near-vision working distance.

The working distance is defined as the distance between the eyes of the wearer and the point fixated by the wearer with his gaze.

In the example more particularly described here, the first working distance is comprised between 20 and 60 centimeters, and is for example equal to 40 centimeters. This first working distance then corresponds to near-vision work.

As a variant, it is possible to envision implementing the method according to the invention for a first working distance comprised between 60 centimeters and 1.5 meters, this corresponding to intermediate-vision work, or between 1.5 meters and infinity, this corresponding to far-vision work.

More precisely, here, in step a), the operator asks the wearer to preferably perform a task chosen from the following tasks:

a reading task;
a writing task;
an interactive task; and
an observation task.

To execute this task, the wearer is presented with a medium 20 (FIG. 1) that he may hold between his hands and place in the way that he desires relative to his head.

This medium 20 is preferably a flat medium including a digital display portion. It is for example preferably a touch tablet.

This medium 20 generally includes a target C1, C2 that the wearer must follow with his gaze during the task that is assigned to him.

For example, for a reading task, the target is made up of each word of the text displayed on the medium.

It may for example be a question of a text displayed on a screen in a black color with, in another color, or highlighted, or underlined, the word to read, which moves along the text.

The wearer reads at each instant the word signaled by the different color of the text, the highlighting or the underlining.

For a writing task, it may this time be a question of words to be written.

The writing task is for example carried out using a stylus on the touch tablet forming the medium 20. It is then possible to directly identify the location that the wearer looks at as he writes as being the point of contact between the end of the stylus and the active screen of the touch tablet.

By "interactive task" what is meant is a task such as an interactive game, in which the target C1, C2 consists of an image that the wearer must follow with his eyes. The interactivity is related to the fact that the wearer must act, for example, click on the medium, depending on various characteristics of the target: position, orientation, contrast, etc.

It is possible for example to envision the target C1, C2 being formed by the image of an arrow and the wearer clicking on the medium 20 on the right or left depending on the direction of the arrow.

The target C1, C2 could also move over the display portion of the medium, in a straight line, the wearer having to click before it touches the edge of this display portion.

The target C1, C2 may also consist of a flashing luminous image, the contrast of which gradually increases. The wearer clicks on the medium as soon as he sees the target appear.

By observation task, what is meant is a task during which the wearer follows with his eyes the target C1, C2, for example an image, without interacting therewith.

Generally, whatever the task in question, it is possible to envision carrying out an adjusting step prior to carrying out the task itself in order to adjust the displayed dimensions of the target C1, C2 on the medium 20 depending on the acuity of the wearer.

It is thus possible to ensure that the wearer is able to distinctly see the target during the task to be carried out, no matter what equipment he has at his disposal at the moment he performs this task.

Preferably, in step a), the frame 10 chosen by the wearer is placed, with no lenses fitted therein, on his head (FIG. 1).

It is also possible to envision placing on the head of the wearer a frame other than that chosen, preferably having dimensions larger than that chosen so that the gaze of the wearer is not constrained by the edges of the frame.

It is likewise possible to envision placing on the head of the wearer the chosen frame with presentation lenses, having no power, or with corrective lenses, for example lenses similar to those that the wearer currently uses.

The frame 10 is preferably equipped with a locating system 40 intended to allow the position of the head of the wearer in space to be determined from a captured image of the head of the wearer equipped with the locating system. This locating system 40 is described in detail in document FR2914173, page 7, line 5 to page 10, line 8. It will therefore not be described in more detail here.

This locating system 40 has predetermined geometric characteristics, which allow, from a captured image of the head of the wearer, in which image this locating system appears, the position and the orientation of the head of the wearer in space to be determined in the frame of reference associated with the image-capturing device. This locating system 40 therefore allows the position and orientation of the frame of reference associated with the head of the wearer to be determined in the frame of reference associated with the image-capturing device.

It is also possible to envision the frame itself, placed on the head of the wearer, playing the role of the locating system.

It is also possible to envision placing on the head of the wearer neither a frame nor lenses. In this case, the head of the wearer may be directly equipped with the locating system.

Step b)

In order to allow the directions of the gaze of the wearer at the first working distance to be determined while the latter is executing the visual task that has been assigned to him, the medium 20 includes at least one image-capturing device 21.

It is preferably a video camera in order to acquire a video of the wearer during the visual task.

The position of the target C1, C2 that the wearer follows with his eyes during the visual task is known at every instant relative to the medium 20. Said position is therefore known in the frame of reference associated with the image-capturing device 21.

Thus, by virtue of this arrangement, the position of the target C1, C2 on which the gaze of the wearer is fixated at the moment of the image capture is known in the frame of reference associated with the image-capturing device and therefore in the frame of reference associated with the head of the wearer.

In step b), an image of the head of the wearer is then captured, using this image-capturing device 21, for various positions of the target C1, C2 corresponding to various gaze directions D1, D2 at the first working distance.

The image-capturing device and the displaying means of the display portion of the medium 20 are preferably synchronized so that the capture of an image is triggered when the target C1 is in a predetermined position, or so that the position of the target C1 in the frame of reference associated with the image-capturing device at the moment of the image capture is memorized and associated with the image captured at this moment.

As mentioned above, the image acquisition may be carried out via the recording of a video.

It is also possible to envision, in the case of an interactive task, the image-capturing device 21 being configured to record an image of the head of the wearer only when the latter clicks on the medium 20.

The captured images of the head of the wearer are transmitted to an information-processing unit that may be integrated into the medium or be remote.

The captured images may be processed in real-time or after all the images have been captured.

From these captured images, the processing unit determines the position of the rotation center CRO of at least one eye of the wearer in the frame of reference associated with the head of the wearer.

The principle of this determination is known per se and for example described in document FR2914173, an equivalent of which in English is the document US20100128220.

By way of example, it is possible to identify the images of a notable point of the eye of the wearer, for example of the pupil of the eye of the wearer, in two images captured while the wearer was fixating his eyes on targets C1, C2 having a different position relative to the image-capturing device. The position of the pupil of the eye relative to the image-capturing device is then determined depending on geometric characteristics of the image of the locating system 40 in these two images. These geometric characteristics provide access to a scale factor of the image and to the rotation angles of the head of the wearer relative to the image-capturing device 21.

The position of the target C1, C2 fixated with the gaze during the two image captures being known relative to the image-capturing device, the position of the eye rotation center CRO is deduced therefrom as being the intersection of the straight lines passing through the target and the pupil of the eye for each captured image.

It is also possible to determine for each gaze direction the corresponding posture of the head of the wearer, i.e. its position and its orientation in the frame of reference associated with the image-capturing device. A data pair associating the posture of the head and the gaze direction is placed in memory in a file.

According to a first embodiment of the method according to the invention, the information-processing unit deduces therefrom the direction D1, D2 of the gaze at the first working distance of the wearer in the frame of reference associated with the head of the wearer during each image capture as being the straight line connecting this rotation center CRO with the target C1, C2 in its corresponding position during the image capture.

As a variant, the position of the eye rotation center CRO of the wearer in the frame of reference of the head of the wearer may be predetermined. To do this, the image processing and capturing steps may be carried out prior to the implementation of the method according to the invention, optionally in one place or by virtue of a different measuring apparatus.

In this case, the position of the eye rotation center CRO of the wearer may be placed in memory manually or transmitted directly to the information-processing unit.

According to a second embodiment, in step b), the position of the eye rotation center CRO is determined depending on a predetermined average position of this rotation center, for example relative to the back face of the ophthalmic lens. To this end, the rotation center may for example be considered to be located at an average distance equal to 27 millimeters from the back face of the ophthalmic lens.

As a variant, it is also possible to measure a reference position of the rotation centers of the eyes in the frame of reference associated with the head of the wearer in a preliminary step, using a method known per se, to record and to transmit this reference position to the information-processing unit.

According to a third embodiment, in step b) each image of the wearer is captured when the target C1, C2 is found on the optical axis of the image-capturing device. Here, an alternative arrangement in which the image-capturing device is placed behind the display portion of the medium 20 is envisioned. The visual task of the wearer is then preferably an observation task during which he follows the target C1, C2 with his eyes. The movement of this target is parameterized so that it passes several times in front of the image-capturing device located therebehind, and the image capture is triggered at the instants corresponding to these passages.

It may for example be a question of writing or reading tasks such as described above, during which the target is formed either by a word signaled by a color, highlighting or underlining (reading task), or by the point of contact of the stylus on the tablet during the writing of a word (writing task).

The position of the sighted point fixated by the wearer with his eyes is thus precisely known.

It is then possible to directly determine the position of the point of intersection of the gaze direction and the ophthalmic lens or the mean plane of the rim of the frame as being the position of the image of the pupil of the eye of the wearer relative to the image of the ophthalmic lens in the captured image. For example, the position of the image of the pupil relative to the image of the rims of the frame is determined. Having done this, the direction of the gaze is determined in step b) as being the straight line connecting the pupil of the eye of the wearer and the pupil of the image-capturing device, which here passes through the target. The surface associated with the frame or with the ophthalmic lens is defined in step c) as being coincident with the image-capturing plane. The eye rotation center is not determined.

Alternatively, it is possible to envision the image-capturing device moving so that the target always remains on its optical axis.

The position of the pupils of the eyes of the wearer relative to the locating system 40 or to the frame 10 is then determined from captured images of the head of the wearer, the direction of the gaze of the wearer at the first working distance being deduced therefrom as the straight line connecting the pupil to the target C1, C2. The eye rotation center is not determined.

According to one variant of each of the embodiments described above, in the case where the wearer is equipped with a frame and corrective ophthalmic lenses, i.e. lenses having a predetermined power, in step b) the processing unit is preferably programmed to determine the position of the eye rotation center of the wearer in the frame of reference associated with the head of the wearer and to deduce therefrom the direction of the gaze at the first working distance as being the optical path connecting the eye rotation center and the target while taking into account the prismatic deviation of the corresponding corrective ophthalmic lens.

It is then a question of taking into account the prismatic deviation, on the one hand, during the determination of the position of the eye rotation center and, on the other hand, during the determination of the gaze direction at the first working distance.

This gaze direction is typically determined by a calculation of the path traced by light rays between the eye rotation center and the target, taking into account this prismatic deviation. In order to perform this calculation of the path traced by light rays, the position of the corrective ophthalmic lens relative to the head of the wearer is taken into account.

Step c)

In order to determine the position of the point of intersection I1, I2, I3, I4 of the direction D1, D2 of the gaze of the wearer at the first working distance determined in step b) and a surface PM or a line associated with said frame or with an ophthalmic lens equipping said frame in step d), the position of this surface or this line in a frame of reference associated with the head of the wearer is determined.

Firstly, the surface or line considered may be defined in various ways.

Preferably, the surface or the line considered is associated with at least one of the rims of the frame. It is thus a question of a surface or a line representative of the position of this rim of the frame when the latter is placed on the head of the wearer.

The expression "associated with at least one of the rims of the frame" is here understood to mean the fact that this surface or this line forms an areal or linear model of at least one of the rims of the frame.

As described here with reference to step a), in the example described here the wearer is more particularly considered, for the implementation of this method, to be equipped with the frame 10 that he has chosen, without ophthalmic lenses fitted in the interior of the rims of this frame.

In this example, the surface considered in step c) will preferably be the mean plane PM of the rim of the frame 10 placed in front of the eye in question of the wearer.

However, as a variant, it may be a question of the mean plane of the two rims of the frame.

It may also be a question of a plane associated with the locating system 40 placed on the frame 10.

As yet another variant, it may be a question of the mean surface of the ophthalmic lens intended to be fitted into the rim of the frame 10 or of the back or front face of this ophthalmic lens.

The surface considered may therefore be flat, as is the case of the mean plane of the rim(s) of the frame or of the lens, or curved, as is the case of the mean surface of the corresponding ophthalmic lens.

When a line associated with the frame or with the ophthalmic lens equipping this frame is considered, said line may be a curved or straight line.

It may in particular be a question of the intersection between, on the one hand, a plane parallel to the sagittal plane of the head of the wearer or the plane called the "Frankfurt plane", and, on the other hand, the surface associated with the frame or with the ophthalmic lens such as defined above.

The Frankfurt plane PF of the head of the wearer is defined as the plane passing through the lower orbital points OR and the porion PO of the wearer, the porion being the highest point in the skull of the auditory canal, which corresponds to the tragion of the ear.

When the wearer is in a natural posture, this Frankfurt plane PF is substantially horizontal.

This is the case for example when the wearer is in a seated or standing configuration in which his head is straight and he is looking straight ahead, into the distance, i.e. preferably at the horizon. The wearer is also said to adopt an orthostatic position, or a position in which he makes a minimum of effort.

The sagittal plane of the head of the wearer is defined as being the plane perpendicular to the Frankfurt plane passing through the bisector of the two eyes. The bisector of the eyes is the axis passing through the middle of the segment defined by the rotation centers of the two eyes and parallel to the Frankfurt plane.

The position of the considered surface, here for example the mean plane PM of the rim of the frame, or of the line may either be determined from the images captured in step b), simultaneously, before or after the processing of these images to determine the gaze direction of the wearer at the first working distance, or be predetermined prior to step d).

In one example illustrating the first case, the position of the mean plane PM of the rim of the frame 10 in the frame of reference associated with the head of the wearer is determined depending on the image of the frame and/or of the ophthalmic lens in the captured image and depending on the corresponding image of the locating system 40. In this case, the information-processing unit also deduces therefrom the position of the considered surface in the frame of reference of the image-capturing device, by the same means.

In one example illustrating the second case, the operator carries out, prior to step d), and preferably before steps a) and b), a calibrating step, in which he determines the position of this mean plane PM by any method known to those skilled in the art. It is for example possible to envision this position being determined from a captured profile image of the head of the wearer equipped with the frame.

It is also possible to envision this position of the considered surface—mean plane of the rim(s) of the frame, mean surface or face of the ophthalmic lens—or of the considered line in the frame of reference associated with the head of the wearer to be obtained from a predetermined database including average positions of the considered surface or line. This in particular is applicable to the case where no frame or ophthalmic lens is placed on the head of the wearer in step a). Then in step c) a virtual fitting of the head of the wearer is carried out, the frame or the ophthalmic lens on the head of the wearer being replaced virtually by virtue of information obtained from the database.

When it is a question of determining the position of said line associated with the frame or with the ophthalmic lens, it is more particularly possible to carry out this step on the basis of a profile image of the wearer equipped with the frame. This profile image is preferably captured before implementing the other steps described here. The considered line then for example corresponds to the intersection between the mean plane of the rims of the frame and the image-capturing plane, which here is parallel to the sagittal plane of the head of the wearer.

This line is then inclined, in the natural posture of the wearer, by an angle relative to the vertical direction equal to the pantoscopic angle of the frame.

It is also possible to determine this line associated with the frame or with the ophthalmic lens as being the intersection between one of the surfaces defined above and the Frankfurt plane of the head of the wearer. The position of the Frankfurt plane is predetermined or determined from captured face-on and/or profile images of the wearer.

Lastly, it is possible to envision the orientation of the considered surface or of the considered line being known in the frame of reference of the head of the wearer, after a calibrating step, for example determined from a captured profile image of the head of the wearer equipped with the frame.

In order to precisely place this surface or this line relative to the head of the wearer during the visual task of the wearer, in step c) the position of at least one reference point associated with the frame or with the ophthalmic lens is then determined in the frame of reference of the head of the wearer from the images captured in step b). The position of the considered surface or of the considered line is thus determined with precision for each captured image.

As a variant, the considered surface or the considered line may be offset, i.e. extend in a plane or in a direction parallel to one of the surfaces or to one of the lines defined above.

Step d)

In step d), the information-processing unit is programmed to determine for each direction D1, D2 of the gaze at the first working distance determined in step b), the intersection between this direction of the gaze and said surface, so as to establish a map of these points of intersection I1, I2, I3, I4 on this surface.

The position of the considered surface, here the mean plane of the rim of the frame, being known relative to the head of the wearer, and the position of the head of the wearer being known in the frame of reference of the image-capturing device by virtue of the locating system 40, the information-processing unit deduces therefrom the position of this mean plane PM in the frame of reference of the image-capturing device 21.

Next, the image-processing unit determines by calculation the intersection of this mean plane PM and of the gaze direction D1, D2 at the first working distance.

To this end, it determines the coordinates (x,y) of the point of intersection I1, I2, I3, I4 of the gaze direction D1, D2 and of the mean plane PM of the rim of the frame 10 in an orthonormal coordinate system (X,Y) of this mean plane PM.

Here, in this orthonormal coordinate system (X,Y), the Y-axis corresponds to the projection of the vertical direction onto the mean plane PM of the rim of the frame 10. The X-axis is an axis perpendicular to the Y-axis, in this mean plane PM.

It is also possible to use the coordinate system of the standard called the "boxing system", with the axes of symmetry of the frame 10 or of the locating system 40.

Step e)

In step e) the information-processing unit determines at least one of the following quantities:
- a mean value of the drop angle A1, A2 of the near-vision gaze;
- the dimensions and the position of a zone of use ZU of the ophthalmic lens containing the determined positions of all the points of intersection I1, I2;
- a position of the centroid of the zone of use ZU;
- the distribution of the positions of these points of intersection I1, I2 in this zone of use.

The drop angle of the gaze is defined as the angle between the projection of the gaze direction at the first working distance determined in step b) and a predetermined primary gaze direction DPR.

This predetermined primary gaze direction DPR corresponds to the gaze direction of the wearer under far-vision conditions, i.e. at a second working distance corresponding to far vision.

To determine it, the operator carries out a step a') in which he places the wearer in a situation in which he performs a visual task at a second working distance.

To do this, he for example asks the wearer to look far away, i.e. to fixate a point distant by at least 5 meters from this wearer.

In a step b'), during this far-vision visual task, at least one direction of the gaze of the wearer is determined at this second working distance.

Preferably, in step b), at least four gaze directions are determined at the first working distance. Four points of intersection I1, I2, I3, I4 are deduced therefrom (FIG. 2).

Preferably, the at least two gaze directions at the first working distance are spaced apart by a nonzero angle in a horizontal direction, which here corresponds to the X-axis of the orthonormal coordinate system of the mean plane PM of the rim of the frame 10. Preferably, the at least two gaze directions at the first working distance are spaced apart by a nonzero angle in a vertical direction, which here corresponds to the Y-axis of the orthonormal coordinate system of the mean plane PM of the rim of the frame 10.

Furthermore, said gaze directions at the first working distance all here correspond to a near vision of the wearer.

Again preferably, in order to obtain points of intersection representing as best as possible the zone of use ZU, said gaze directions at the first working distance are spaced apart by at least 5 degrees of angle in the frame of reference of the image-capturing device.

Preferably, said gaze directions at the first working distance are spaced apart by at least 15 degrees of angle for a visual task distributed over a measuring surface of 17 centimeters width by 24 centimeters length and carried out at a working distance equal to 40 centimeters.

In practice, a number of points of intersection comprised between 2 and 500 points and preferably between 50 to 250 and preferably higher than 10 points is preferably determined.

It is thus for example possible to determine an average value of the drop angle of the gaze as being the arithmetic mean of the values of the drop angle of the gaze determined for each gaze direction at the first working distance determined in step b).

A zone of use ZU may be determined so as to encompass all the determined points of intersection I1, I2, I3, I4.

It may be a question of an ellipse or a rectangle that contains all or a percentage of the determined points of intersection. Preferably, the outline of the zone of use ZU surrounds at least 95% of the determined points of intersection.

The distribution F1, F2 (FIGS. 3 and 4) of the points of intersection determined in step d) in this zone of use ZU may for example be determined along the Y-axis of the orthonormal coordinate system (X,Y) of the mean plane PM. It is then for example a question of referencing each point of intersection by its coordinate along this Y-axis and of counting the number of points of intersection, the corresponding coordinate of which is comprised in a given interval of coordinates.

The curve giving the number of points of intersection as a function of the coordinate along the Y-axis is then traced in order to obtain the distribution F1, F2 of the points of intersection.

It is also possible to determine a dispersion of the points of intersection.

To this end, the coordinates (xm, ym) of the centroid of the points of intersection I1, I2, I3, I4 are determined and the dispersion relative to this centroid is calculated using a conventional variance, standard-deviation, error, etc. type formula.

Furthermore, in step e), the information-processing unit determines at least one of the following optical conception parameters: progression length LP, inset E, reading distance or position of the near-vision zone.

This determination is for example carried out depending on one of the determined quantities defined above.

The progression length LP may for example be determined depending on the average value of the drop angle A1, A2 of the near-vision gaze.

The progression length LP is for example determined depending on the size of the zone of use ZU along the vertical Y-direction and/or on the distribution of the points of intersection in the zone of use along this direction.

In particular, generally, the larger the determined zone of use, the smaller the deduced progression length.

Furthermore, the determined progression length LP also takes account of the shape of the rims of the chosen frame.

The total height of the rim of the chosen frame 10 may be input by hand, determined from a digitization of the frame or extracted from a predetermined database.

The vertical spread of the zone of use, i.e. the size of the zone of use along the vertical Y-direction of the lens may thus allow the progression length LP to be adjusted so as to raise the near-vision zone, such that the latter is included in the ophthalmic lens. This correction of the progression length increases in magnitude as the vertical spread increases in size in order to provide a large near-vision zone that is easily accessible and suitable for the visual behavior of the wearer.

In another example, the position of the centroid of the zone of use and the vertical spread of the zone of use ZU allow the height of the near-vision zone 12 to be determined.

The distribution of the points of intersection in this zone of use may also allow the deduced progression length to be determined.

By way of example, the method according to the invention may make it possible to choose between two progression lengths for example equal to 14 and 18 millimeters.

For example, the position in x and/or in y of the centroid of the zone of use is used to determine the position in x and/or in y of the near-vision reference point IVP of the progressive lens.

The far-vision reference point being predetermined, it is possible to deduce therefrom the value of the corresponding inset E.

In another example, the high limit of the zone of use is used to adjust the progression profile to 85% spherical power addition, which corresponds to the start of the near-vision zone 12, by modifying the progression profile of the design so as to deliver a near-vision zone 12 that is consistent with the visual behavior of the wearer.

In addition, provision may be made for the progression length LP to be adjusted so that the centroid of the zone of use corresponds to an addition of 100%, i.e. forms part of the near-vision zone 12. In the exemplary implementation described here, the determined zone of use is located in the near-vision zone of the ophthalmic lens of the wearer.

Thus, the gaze directions of the wearer at the first working distance, which directions are used to determine the group of points of intersection, in order to deduce therefrom this zone of use, are near-vision gaze directions.

As a variant, it is also possible to carry out analogous measurements for the far vision or the intermediate vision of the wearer.

It is then a question of for example determining a group of points of intersection with far-vision gaze directions. The far-vision gaze directions are then spaced apart by an angle of at least 5 degrees.

It will be understood that the far-vision gaze directions are spaced apart by at least 5 degrees of angle from the near-vision gaze directions.

Lastly, the optical conception parameter determined in step e) may comprise an amplitude of the movement of at least one eye of the wearer during the reading task and/or an amplitude of the movement of the head of the wearer during the reading task, and/or an eye-head coefficient equal to the ratio of the amplitude of the movement of an eye of the wearer in a determined direction to the maximum amplitude of the movement of this eye during the reading task.

To this end, in step a), the wearer is placed in a situation in which he performs a predefined reading task.

This reading task involves reading at least one paragraph including a plurality of lines, for example 4 or 5 lines, from left to right or from right to left depending on the language in question.

It is observed that the wearer adopts an increasingly natural position as he reads and especially when he changes page.

Therefore, preferably, a text including a plurality of pages is used, and more particularly the measurements corresponding to the last pages read are exploited.

The steps b), c) and d) are carried out such as described above, so as to determine a near-vision zone of use of at least one of the ophthalmic lenses intended for the frame chosen by the wearer.

In step e), the dimensions of said zone of use and in particular a width of the zone of use measured in a horizontal direction and a height of the zone of use measured in a vertical direction of the lens are determined.

The angular amplitude of the movement of the eyes of the wearer during the reading task, in the horizontal direction and in the vertical direction, is deduced therefrom.

Preferably, the measurement is carried out for each of the eyes of the wearer so as to determine the dimensions of the zones of use of the left and right ophthalmic lenses intended to equip this wearer.

Since the position of each eye rotation center relative to the ophthalmic lens is known, the angular amplitudes of the movement of the right eye and of the left eye may be deduced therefrom. Specifically, it is possible for example to consider the eye rotation center to be located on average 27 millimeters from the back face of the ophthalmic lens.

Since the dimensions of the text displayed on the medium and read by the wearer, and the reading distance of the wearer, i.e. the distance between the eyes of the wearer and this text, are known, the maximum angular amplitude of the movement of each eye is preferably determined as being the angular extent of the text seen by the wearer, in the horizontal or vertical direction in question.

The difference between the maximum angular amplitude of movement of the eyes and the angular amplitude of the measured effective movement of the eyes in fact corresponds to the amplitude of the movement of the head of the wearer during the reading. It is therefore also possible to deduce this parameter from the determined zone of use.

By dividing the angular amplitude of the movement of each eye by the maximum angular amplitude of the movement of each eye, a coefficient called the eye-head coefficient, which is characteristic of the behavior of the wearer during a reading task, is deduced therefrom.

This coefficient quantifies the propensity of the wearer to move his eyes or his head during the reading task.

It is important to take it into account as regards the optical design of the lens, especially when determining the near-vision zone of the lens.

A wearer having an eye-head coefficient close to 1 will be correspondingly more at ease in near vision if the near-vision zone is large.

Provision may therefore be made to determine, in step e), the progression length and/or the position and dimensions of the near-vision zone depending on this coefficient.

It is also possible to determine the average of the angular amplitude of the movement of the eye as being the average of the angular movements of the left eye and right eye of the wearer. It is then possible to deduce therefrom an average eye-head coefficient.

As a variant, it is also possible to follow the movement of the head by virtue of the image-capturing device and to determine directly the angular amplitude of the movement of the head during the reading.

This taking into account of the eye/head behavior of the wearer makes it possible to ensure an optimal visual comfort for this wearer.

Here, one particular exemplary device for implementing the method according to the invention has been described. More generally, such a measuring device including:
- image-capturing means; and
- means for displaying a moving target, the position of which is known in a frame of reference associated with the image-capturing device, said means being programmed to record, on each image capture, the corresponding position of the target on the displaying means or being programmed to trigger an image capture when the target has a predetermined triggering position on the displaying means, may allow this method to be implemented.

This measuring device especially includes means for synchronizing the display of the target and the capture of an image.

The invention claimed is:

1. A method for determining at least one optical conception parameter of a progressive ophthalmic lens intended to equip a frame chosen by a wearer, depending on the visual behavior of the latter, comprising the following steps:
   a) placing the wearer in a situation in which he performs a visual task at a first working distance, wherein, in step a), the wearer follows with his eyes a target, the position of which is known in a frame of reference associated with an image-capturing device;
   b) determining, during this visual task, at least two directions of the gaze of the wearer at this first working distance in a frame of reference of the head of the wearer;
   c) determining a relative position of a surface or a line associated with said frame with an ophthalmic lens intended to equip said frame in this frame of reference of the head of the wearer, and wherein in step b), using this image-capturing device, an image of the head of the wearer is captured for various positions of the target corresponding to the various gaze directions at the first working distance and wherein, in step b), for each image captured while the wearer is equipped with the frame fitted with ophthalmic lenses, the position of the rotation center of at least one eye of the wearer is determined in the frame of reference associated with the head of the wearer and therefrom the direction of the gaze at the first working distance is deduced as being the optical path connecting the rotation center of the eye and the target, while taking into account the prismatic deviation of said ophthalmic lens;
   d) determining, for each direction of the gaze at the first working distance determined in step b), the intersection between this direction of the gaze at the first working distance and said surface or said line, so as to establish a map of these points of intersection with said surface or said line; and
   e) deducing from this map said sought optical conception parameter.

2. The method as claimed in claim 1, wherein, in step a), the first working distance is a near-vision distance and the wearer performs a reading or writing task or an interactive task or an observation task.

3. The method as claimed in claim 1, wherein, in step c), said surface is one of the following surfaces: mean surface of the ophthalmic lens, mean plane of a rim of the frame, mean plane of the rims of the frame, back or front face of the ophthalmic lens.

4. The method as claimed in claim 1, wherein, in step b), for each captured image, the position of the rotation center of at least one eye of the wearer is determined in the frame of reference associated with the head of the wearer and therefrom each direction of the gaze at the first working distance is deduced as being the straight line connecting this rotation center with the target in its corresponding position.

5. The method as claimed claim 4, wherein, in step b), the mean position of the rotation center of the eye of the wearer is approximately estimated in the frame of reference associated with the head of the wearer.

6. The method as claimed in one of claim 4, wherein, in step b), a reference position of the rotation centers of the eyes is measured in the frame of reference associated with the head of the wearer in a preliminary step and this reference position is recorded.

7. The method as claimed in claim 1, wherein, in step b), each image of the wearer is captured when the target is found on the optical axis of the image-capturing device.

8. The method as claimed in claim 7, wherein, in step d), the intersection between the direction of the gaze at the first working distance and said surface is determined by directly measuring in the captured image the position of the image of the pupil of the eye of the wearer in the image of the ophthalmic lens.

9. The method as claimed in claim 1, wherein, in step a), the wearer is equipped with the chosen spectacle frame and, in step c), the position of said surface or said line is determined in the frame of reference of the head of the wearer from at least one captured image of the head of the wearer during said visual task.

10. The method as claimed in claim 1, wherein, in step c), the position of said surface or said line is determined in the frame of reference of the head of the wearer from a database.

11. The method as claimed in claim 1, wherein, in step e), at least one of the following quantities is determined: a mean value of the drop angle of the near-vision gaze, the dimensions and/or the position of a zone of use of the ophthalmic lens containing the positions of at least some of the determined points of intersection, the distribution of the positions of these points of intersection in this zone of use.

12. The method as claimed in claim 1, wherein, in step e), at least one of the following optical conception parameters is determined: progression length, and/or inset and/or reading distance and/or position of the near-vision zone.

13. The method as claimed in claim 1, wherein at least two said gaze directions at the first working distance are spaced apart by at least 5 degrees of angle in projection in a horizontal plane.

14. The method as claimed in claim 1, wherein, in step b), at least four different gaze directions at the first working distance are determined, at least two of which are spaced apart by a non-zero angle in a horizontal direction.

15. The method as claimed in claim 1, wherein, in step a), the wearer performs a near-vision visual reading task, and in step e), from the map determined in step d), a zone of near-vision use of the lens, and/or an amplitude of the movement of at least one eye of the wearer during the reading task and/or an amplitude of the movement of the head of the wearer during the reading task, and/or an eye-head coefficient equal to the ratio of the amplitude of the movement of an eye of the wearer in a determined direction to the maximum amplitude of the movement of this eye during the reading task are/is deduced.

16. A measuring device for implementing the method as claimed in claim 1, including:
   image-capturing means; and
   means for displaying a moving target, the position of which is known in a frame of reference associated with the image-capturing device;
   which means are programmed to trigger an image capture when the target has a predetermined triggering position on the displaying means.

17. The method as claimed claim 1, wherein, in step b), the mean position of the rotation center of the eye of the wearer is approximately estimated in the frame of reference associated with the head of the wearer.

18. A method for determining at least one optical conception parameter of a progressive ophthalmic lens intended to equip a frame chosen by a wearer, depending on the visual behavior of the latter, comprising the following steps:
   a) placing the wearer in a situation in which he performs a visual task at a first working distance;
   b) determining, during this visual task, at least two directions of the gaze of the wearer at this first working distance in a frame of reference of the head of the wearer;
   c) determining a relative position of a surface or a line associated with said frame or with an ophthalmic lens intended to equip said frame in this frame of reference of the head of the wearer;
   d) determining, for each direction of the gaze at the first working distance determined in step b), the intersection between this direction of the gaze at the first working distance and said surface or said line, so as to establish a map of these points of intersection with said surface or said line; and
   e) deducing from this map said sought optical conception parameter,
   wherein the following steps are furthermore carried out:
   a') placing the wearer in a situation in which he performs a visual task at a second working distance;
   b') determining, during this visual task, at least one direction of the gaze of the wearer at this second working distance;
   in step e), this gaze direction of the wearer at the second working distance is taken into account to determine said sought optical conception parameter.

* * * * *